United States Patent [19]

Grothoff

[11] 4,321,953

[45] Mar. 30, 1982

[54] METHOD OF DISCHARGING AND APPLYING FLOWABLE MEDIA

[76] Inventor: Gisela Grothoff, Pulverstr. 35, D-4600 Dortmund 50, Fed. Rep. of Germany

[21] Appl. No.: 110,387

[22] Filed: Jan. 7, 1980

[30] Foreign Application Priority Data

Jan. 16, 1979 [DE] Fed. Rep. of Germany ....... 2901433

[51] Int. Cl.³ .............................................. B65B 3/04
[52] U.S. Cl. ............................................ 141/2; 141/3
[58] Field of Search ...................... 141/1, 2, 3, 20, 98, 141/4–12, 250–284, 301, 302

[56] References Cited

U.S. PATENT DOCUMENTS

| 3,857,422 | 12/1974 | Cunningham | 141/3 |
| 4,108,219 | 8/1978 | Shulsinger | 141/3 |

*Primary Examiner*—Houston S. Bell, Jr.
*Attorney, Agent, or Firm*—Michael J. Striker

[57] ABSTRACT

In accordance with a method of discharging and applying a flowable medium under pressure, a charge element, and a discharge element is provided. The discharge element has a storage chamber arranged for receiving the flowable medium and provided with an outlet valve, and a gas chamber arranged for accommodating a pressure gas medium and separated from the storage chamber by a displaceable member allowing to vary the volumes of the chambers. Flowable medium is fed from the charge element element into the storage chamber of the discharge element so that the displaceable member displaces in the direction toward the gas chamber, the volume of the storage chamber increases, the pressure gas medium in the gas chamber is compressed and thereby the flowable medium is stored in the storage chamber under pressure. The flowable medium is discharged from the storage chamber of the discharge element through the outlet valve by reducing the volume of the storage chamber and increasing the volume of the discharge element with displacement of the displaceable member in the opposite direction and simultaneous expansion of the gas medium into the gas chamber of the discharge element.

46 Claims, 3 Drawing Figures

METHOD OF DISCHARGING AND APPLYING FLOWABLE MEDIA

BACKGROUND OF THE INVENTION

The present invention relates to method for discharging and applying flowable media under pressure for cosmetic, pharmaceutic, and technical purposes.

Several methods for discharging and applying flowable media under pressure are known. In accordance with one method a gas stream, for example, compressed air, passes through a nozzle and acts upon a liquid forwarded thereinto so as to break the liquid in form of drops to atomize the same. In order to generate the compressed air, expensive compressors are, however, necessary which involves operation with a stationary equipment. Furthermore, the drops of the broken liquid produced by this method have substantially not uniform dimensions. A portion of the liquid is always broken into drops with small dimensions which do not adhere to surfaces to be treated and contaminate the air as suspended particles. This leads, especially in small spaces, such as for example in barber shops, to bothering of customers and personnel and to dirtying of the equipment. This method makes possible to atomize two or more liquids with separate supply of the same. However, an accurate mixing ratio of the components relative to one another can be attained with difficulties and after complicated and time-consuming adjusting process, and the ratio cannot be reliably reproduced. Also, foaming of the liquids in accordance with this method is not possible. Generally speaking, the implementation of this method in small industrial shops and in household is hardly accepted.

It is further known to pack a liquid preparation together with a liquefied or gaseous motive gas in a pressure atomizing package, and to discharge the same via a discharge head provided with an outlet valve, as spray or as foam. The pressure atomizer packages are convenient, easy to transport and simple to utilize. However, they have the disadvantage in that they are utilized once, and therefore, the costs of the package and the motive gas are considerably high as compared with the costs of the liquid preparation. During the atomization according to this method, suspended particles are also generated which leads, similarly to the air operated atomizing devices, to troubles and contamination in the condition of frequent utilization of the devices. Fluorochlorhydrocarbon compounds which are generally utilized as motive gas are believed to be damaging for the environment. Also, the attempts to separate the motive gas into the pressure atomizer doses by bags or pistons were not successful in practice. In this construction reduction of the quantity of the motive gas and increase of the component of the flowable preparation, as well as the reduction of the quantity of the suspended particles, as compared with the normal spraying nozzles, can be attained. However, the cost of these packages, as compared with the normal aerosol doses, is uneconomically high because of the additional structural parts, the complicated and expensive filling, and the necessity of the utilization of the pressure atomizer doses with high pressure tightness. A further basic disadvantage of the above-described pressure atomizer packages is that in this packaging process it is commercially impossible to utilize slowly interacting materials which must be mixed shortly before the utilization in a predetermined ratio and then discharged as foam, such as for example, hair dyes.

It is further known to atomize liquids with the aid of finger pressure actuated atomizing pumps via a whirling chamber nozzle, in nearly mechanical manner without a motive gas. Such a method has, however, the disadvantage that the finger force becomes weaker very fast and thereby the atomizing is not continuous, but, instead, is intermittent. Therefore, a uniform wetting of the surfaces to be treated cannot be attained. It is also difficult to reach the locations which are not easy of access, for example, to reach the rear head region by hair spray preparations with simultaneous pump movement. The attempts to actuate the atomizing pumps not by hand, but by eccentrics driven by an electric motor, did not show the desirable results. The reason for this is that the weight of the arrangement because of the motor, gearing, batteries and housing makes the same inconvenient, additional motor noise generates, the disadvantageous intermittent atomizing takes place in this method, and the prime cost of the arrangement is too high as compared with the advantages thereof. In order to provide for a continuous spraying process with simultaneous atomizing without a motive gas, a further method was proposed. In accordance with this method, the liquid to be atomized is pumped before the discharge into a chamber which is sealed by a sleeve valve loaded at the opposite side by a prestressed spring. Then, the liquid which is held under pressure acting upon the sleeve valve is atomized via an outlet valve provided with a whirle spray head, until the sleeve valve attains its initial position. This arrangement has, however, the disadvantage in that the liquid pressure provided by the spring is too low for sufficient atomizing and in any event does not reach generally used medium pressure of 6 bar. Also, the liquid pressure decreases with continuous emptying of the storage chamber in correspondence with the decreasing spring action. Thereby, the characteristic of the spring process and also the dimensions of the particles vary during the emptying process, which is not desirable in practice.

A further proposal is known in which, instead of the spring actuated piston, the contraction force of a rubber hollow body with pumped in liquid, is utilized for atomizing the liquid. This proposal is not better than the other proposals. Here also the resulting liquid pressure is too small for acceptable atomizing, it decreases in dependence upon the emptying rate further.

Finally, a method is known in accordance with which the liquid is driven and atomized from a refillable pressure tight container after charging of an air pressure cushion via an outlet valve provided with a whirling spray head. In this arrangement the inner pressure also reduces and the spring characteristics also vary considerably during the emptying process, and the volume of the air cushion amounts to a multiple of the individual volumes of the liquid whereby the container is very heavy and inconvenient to use. This arrangement has a further disadvantage in the fact that, similarly to the mechanically operated intermittent atomizing pumps and the normal pressure atomizer packages, atomization of the liquid can be performed only in approximately vertical position of the package and position-independent atomizing is impossible. Finally, this method similarly to the above-mentioned two methods makes possible discharge of the product only in liquid form but not in foamed form.

SUMMARY OF THE INVENTION

Accordingly, it is an object of the present invention to provide a method of discharging and applying a flowable medium under pressure, which avoids the disadvantages of the prior art.

More particularly, it is an object of the present invention to provide a method of discharging and applying a flowable medium under pressure, which in dependence upon the characteristics of the material and the construction of the outlet mouthpiece, makes possible the discharge and applying of the flowable medium selectively in form of an atomized spray stream, as uninterrupted liquid stream, jet, or drops.

Another object of the present invention is to provide a method of discharging and applying a flowable medium under pressure, which makes possible admixing of liquefied motive gas as an additional component so as to discharge and apply the liquid in foamed form with continuous but dosed and interadjusted discharge ratio.

Still another feature of the present invention is to provide a method of discharging and applying a flowable medium, in accordance with which high and uniform liquid pressure is maintained during the entire emptying process and so that a uniform discharge takes place in each position.

It is a further object of the present invention to provide a method of discharging and applying a flowable medium under pressure, which makes possible mixing of two or more flowable media, with simultaneous admixing of a flowable motive gas if necessary, immediately before the utilization, with high homogeneity and predetermined ratio relative to one another, and to store the thus produced medium for subsequent joint discharge.

Still a further feature of the present invention is to provide a method of discharging and applying a flowable medium under pressure in accordance with which the cost of the individual application relative to the cost of the pressure atomizer package is considerably reduced, damages to environment because of noise, motive gas and suspended particles are eliminated, and the arrangement for performing the method is light, convenient and portable.

Yet a further feature of the present invention is to provide a method of discharging and applying a flowable medium under pressure, which possesses all above-mentioned advantages at the same time.

In keeping with these objects and with others which will become apparent hereinafter, one feature of the present invention resides, briefly stated, in a method of discharging and applying a flowable medium under pressure, which comprises the steps of providing a charge element, and a discharge element having a storage chamber arranged for receiving the flowable medium provided with an outlet valve and a gas chamber arranged for accommodating a pressure gas medium and separation from the storage chamber by a displaceable member allowing to vary the volumes of the chambers, feeding the flowable medium from the charge element into the storage chamber of the discharge element so that the displaceable member displaces in the direction toward the gas chamber, the volume of the storage chamber increases, the pressure gas medium and the gas chamber is compressed, and thereby the flowable medium is stored in the storage chamber under pressure, and discharging the flowable medium from the storage chamber of the discharge elements through the outlet valve by reducing the volume of the storage chamber and increasing the volume of the gas chamber of the discharge element with displacement of the displaceable member in the opposite direction and simultaneous expansion of the gas medium in the gas chamber of the discharge element.

The flowable medium may be fed by a pump unit, and the outlet valve may be provided with an outlet mouthpiece. The displaceable member may be formed as a deflectable diaphragm or membrane, as a movable piston, or as a deformable diaphragm-like hollow body. Gas or a mixture of gases may be utilized as the gas medium. The pump unit may be hand-driven or motor-driven.

The required economy of the method and the reduction of the costs as compared with the pressure atomizer package which is not repeatedly utilized, is attained by that the feeding step and the discharging step are continuously repeated.

When permanent gases which do not liquefy at room temperature are utilized as the pressure medium, the volume of the gas chamber must be many times greater than the volume of the storage chamber in order to avoid high pressure differential between filled and emptied storage chamber. On the other hand, the dimension of the discharge element must be kept as small as possible on the grounds of weight and convenience to handle. Thereby, it is advantageous when gas or gas mixture utilized as the pressure medium in the discharge element is formed by gas liquefiable at room temperature, whose pressure measured in the liquid component at room temperature amounts to between 1 and 15 bar.

In order to guarantee that uniform inner pressure remains in the storage chamber during the entire emptying process, the gas medium in the gas chamber is provided at such a quantity that even when the storage chamber is completely emptied, a small portion of not vaporized liquid gas component is still available in the gas chamber.

In order to produce a multiple component system in which individual components are mixed immediately before the utilization, another feature of the invention is that several pump units are provided which operate with tact synchronization and stroke synchronization and feed flowable media in a predetermined adjustable ratio relative to one another into the discharge element.

Many materials which are formed mainly on water base, must be applied in foamed form. In accordance with the present invention it is provided for this case that one or several flowable foamable media are fed simultaneously with one or several motive gases or motive gas mixtures in a predetermined adjustable ratio relative to one another into the discharge element, separately but with tact synchronization and stroke synchronization.

In order to prevent foaming of the system in the discharge element before the discharge, the pressure which builds in the storage chamber by the mixed liquefied motive gas is smaller than the pressure of the pressure medium developed in the gas chamber. This can be attained by a respective selection of the liquefied motive gas. Homogeneous mixing of the individual components dosed by individual pump units may be attained, in accordance with the applicant's invention, by that the individual streams which exit from the pump units join with one another before entering the storage chamber of the discharge element.

It may also be advantageous to join the individual streams in a mixing chamber provided with a homogenizing member connected with the mixing chamber in series.

It is necessary to determine the quantity of flowable media fed from the pump units into the storage chamber of the discharge element, in accordance with receiving possibility of the storage chamber. This can be attained by provision of a metering element operative for adjustment and limiting of the quantity of the flowable medium which is supplied from the charge element into the discharge element.

When the not fully emptied storage chamber is again filled with new charge, damages to the structural parts resulting from the excessive pressure can take place. In order to avoid this, an excess pressure unit is provided between the charge element and the discharge element. This excess pressure unit performs the functions of switching or opening a return flow from the storage chamber of the discharge element.

In accordance with a further especially advantageous feature of the present invention, a controlling element or giver is provided which is arranged in the discharge element and terminates the feeding process when the flowable medium reaches the nominal volume of the storage chamber of the discharge element.

In accordance with still a further feature of the present invention, an automatically operating backflow blocking element is arranged between the pump units and the storage containers for the flowable medium and the liquefied motive gas as well as the storage chamber.

In accordance with the present invention, the charge element and the discharge element may be assembled in a unit.

However, in order to easily handle the arrangement and to reduce its weight for the user, it is advantageous when the charge element and the discharge element are coupled with one another during the feeding step, and then separated from one another for the discharge of the flowable media.

In accordance with another feature of the present invention the outlet valve of the storage chamber of the discharge element is arranged separate from the supply conduit which extends from the charge element to the storage chamber of the discharge element.

In order to improve the functioning and to reduce the structural elements, it is recommended especially for the arrangement with separate charge element and discharge element, to form the outlet valve simultaneously as a coupling between the charge element and the supply conduit. The outlet mouthpiece of the outlet valve is advantageously exchangeable in order to make possible propagation of the flow media in accordance with different application methods, for example, in form of spray, jet, drops or foam.

In order to utilize the arrangement at narrow locations difficult of access or to provide stationary position of the arrangement with further reduction of weight, the outlet valve with the outlet mouthpiece may be separate from the discharge element and connected with the latter by a flexible conduit.

In accordance with a further advantageous feature of the present invention, an additional intermediate storage element may be provided between the pump units and the discharge element, when the charge element and discharge element are separate from one another. In such a method, the charging process of the discharge element with a respective dimension of the cross-section of the supply conduit between the intermediate storage element and the discharge element is performed faster and without noise as compared with the direct charging the discharge element from the pump units. Thereby, the charged discharge element can be available very fast especially in industrial field.

The intermediate storage element has a construction which corresponds to the functions performed by the discharge element, and is arranged in the charge element.

In accordance with the invention a sufficient pressure drop is provided between the intermediate storage element and the discharge element whereby the highest possible speed of feeding of the discharge element takes place. This is attained by that the pressure medium accommodated in the gas chamber in the intermediate storage element has a higher pressure than that of the pressure medium accommodated in the discharge element. For example, the pressure chamber of the intermediate storage element may be filled with propane with a vapor pressure of 9 bar at 20° C., whereas the gas chamber of the discharge element may contain a gas mixture from 60 weight percent of propane and 40 weight percent of butane with a steam pressure from 6.5 bar at 20° C.

In order to provide the charging of the discharge element in one operation, it is advantageous when the contents of the storage chamber of the intermediate storage element is at least equal to the contents of the storage chamber of the discharge element.

In accordance with a further feature of the present invention, the determination of the process of feeding of the discharge element may be detected by a signalling element or gear which is arranged in the intermediate storage element or between the intermediate storage element and the discharge element.

This can be peformed in form of optical of acoustic signals. Furthermore, the signalling element can also interrupt the feeding process by a valve arranged in the supply conduit between the intermediate storage element and the discharge element.

It is also possible to separate the discharge element completely from the charge element by signals from the signalling element, and to eject the discharge element from the charge element. Further, the signalling element signal can be utilized to actuate the pump unit after the termination of the feeding process, whereby the feeding process is performed in noise-free manner.

Finally, it is advantageous to arrange a detecting element in the supply container or the supply conduit to the pump units, which signals the emptying of the container until the replacement of the emptied container, or automatically switches the pump unit to a replacement container.

The nominal contents of the storage chamber of the discharge element may amount to from several millimeters to several liters, and is specifically limited only by the weight and convenience of the discharge element. Generally, the nominal contents is dimensioned in accordance with the product characteristics of the flowable materials and the consumption requirements depending upon the product. For example, 20 milliliter contents is sufficient for mouth spray and perfume spray, whereas for body spray 200 milliliter and for hair spray 400 milliliters are to be provided. Further, the contents of the discharge element is determined in accordance with the requirements made to the feeding of a specific product. For example, an exactly determined quantity of hair dyes or hair medications must be provided for each treatment. In addition to the commercial advantages, the method in accordance with the present invention has the advantage in that during the discharge of the flowable medium through the discharge element no motive gas is released into the surrounding atmosphere. Only when the medium is discharged in form of foam, a small amount of the motive gas is released. Here, a gas which is acceptable on the environment protection grounds can be utilized, such as for example butane. The consumption of the motive gas is small, inasmuch as an addition of 0.5 percent of motive gas to the flowable medium provides for sufficient generation of foam. In contrast to the pressure atomizing packages, the addition of the motive gas in accordance with the present invention may provide for adjustment of the quality of foam and the intensity of the foaming process. It has been shown that in the case of floable media which are difficult to atomize, the atomization is favorably influenced by the addition of the liquefied motive gas and the dimension of the particles is further reduced. The quantity of the pressure medium to be filled in the discharge element is also small. For example, only 0.6 gram of butane gas can be contained in 100 milliliter under its own pressure. With reserve in liquid component and with adjustment to losses during long time storage, 1.2 gram of butane per 100 milliliter of contents in the discharge element is sufficient. This quantity is so small that in the event of breakage of the discharge element, a danger for the user or for the surrounding atmosphere does not take place.

Essential objects and economical basis of the present invention are that the discharge element is continuously refilled. The manufacturing cost of the discharge element is higher than that of the pressure atomizing package which is used only one time, and it includes also the cost of the required charge element. However, in the long run the cost of maintenance in the inventive method is smaller because of the economy of motive gas and the package materials as compared with the pressure atomizing packages. The flowable materials in the desired product form are required for charging of the charge element, which materials can be supplied in inexpensive big packages. It is, however, advantageous to provide individual discharge elements for the different products, in order to eliminate cleaning of the discharge part before charging the same with a new different product. The preliminary cleaning for changing the product can be avoided either constructively by the avoidance of dead spaces and smallest possible conduit cross-section, or by the peformance of a flushing of the charge element with a neutral liquid. In private households with only small consumption, when the supply of the charge element is hardly beneficial there is the possibility of the recharge by arrangement of automatic machines with integrated charge elements for example in consumer markets. Different products can be recharged with automatic determination of the products and the quantities by the utilization of specific coding marks on the discharge elements. Simultaneously, the automatic machines can test the functions and safety of the discharge elements and sort out damaged packages. It is also possible to exchange empty discharge elements by the automatic machines for filled packages and then to load the same at a central location, to proof the same, and further to introduce them into the cycle. The cost in this case is, however, increased as compared with the direct charging.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF PREFERRED EMBODIMENTS

Figure 1:
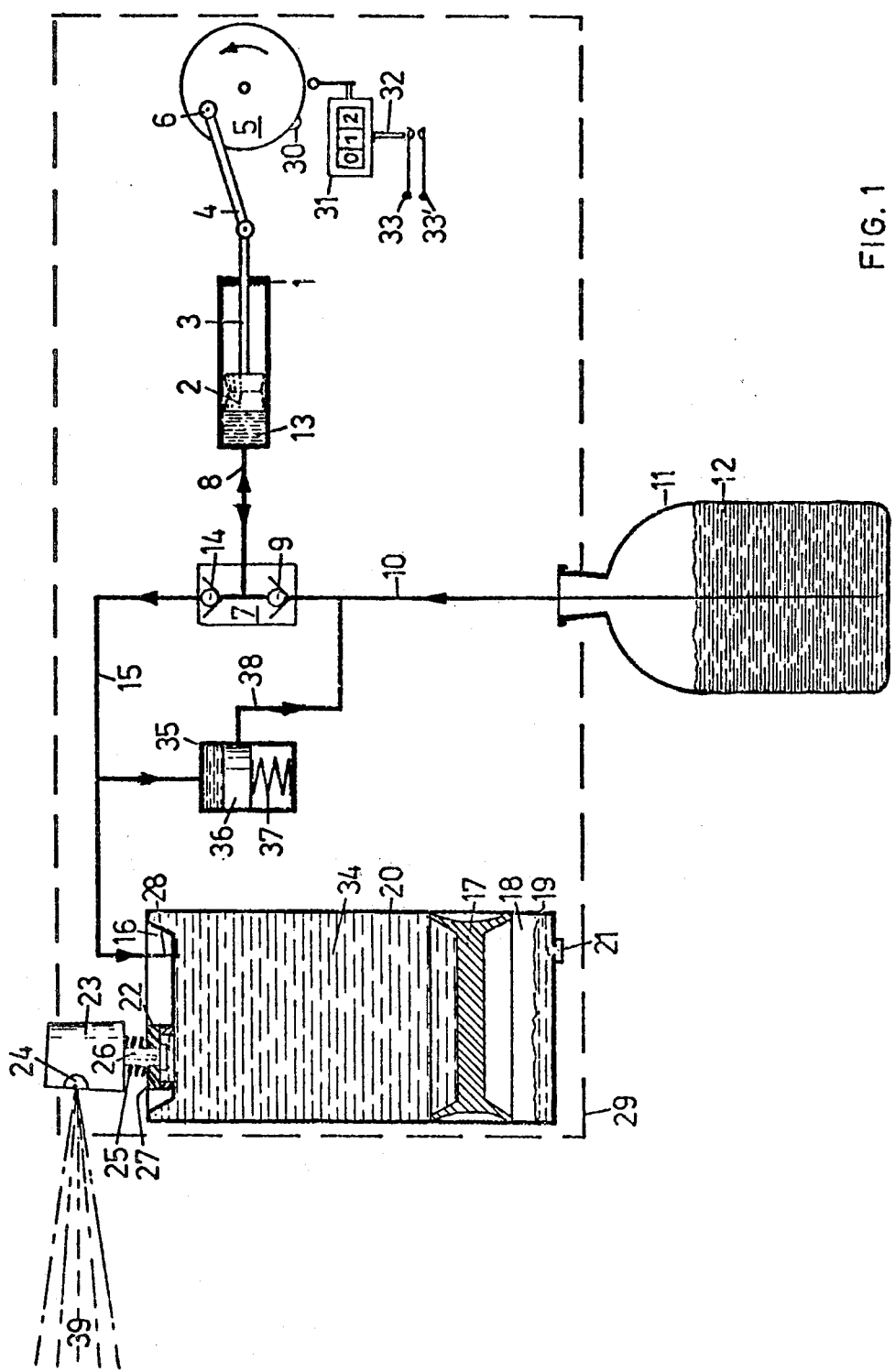
FIG. 1 is a schematic view showing a charge element with a pump unit and a discharge element with a displaceable piston forming a locking element between storage and gas chambers.

A method of discharging and applying a flowable medium under pressure is illustrated as performed by an arrangement shown in the drawing. The arrangement in accordance with one embodiment shown in FIG. 1 has a pump unit 1 with a piston 2 and a piston rod 3. The piston rod 3 is driven in reciprocating movement by a connecting rod 4 and a crank disc 5 with an eccentrically arranged crank pin 6. The crank disc 5 is driven in rotation by a not shown driving element, for example an electric motor. During each revolution of the crank disc, the piston 2 displaces so as to perform a suction stroke and a compression stroke.

A valve element 7 is connected in series with the pump unit and communicates with the latter by a conduit 8. The valve element 8 has a lower valve member 9 which opens during the suction stroke of the pump unit and thereby a flowable medium 12 accommodated in a storage container 11 is aspirated through a conduit 10 into a piston chamber 13. During the compression stroke, the valve member 7 is automatically blocked, and simultaneously a valve member 14 opens for a period of time corresponding to the compression stroke. Thereby the medium located in the piston chamber is fed through a conduit 15 into a discharge element 16, a movable piston 17 in the discharge element 16 displaces against the action of a liquefied motived gas 19 accommodated in a gas chamber 18, and a pressure is applied to the motive gas.

The piston 17 runs in a pressure-tight container 20 which is provided wih a bottom opening 21 for single filling of the liquefied motive gas, and with an outlet valve 22. The latter includes an outlet mouthpiece 23 with a spraying nozzle 24, a pressure spring 25, a valve member 26, and a seal 27. As shown in this Figure, the charge part and the discharge part are fixedly connected with one another by a connection 28 and together form a unit which is accommodated in a case schematically shown by lines 29.

The number of the pump strokes and thereby the quantity of the medium supplied by the pump unit 1, the quantity being determined by the piston area and stroke length, is registered, for example, by a meter 31 which operates from a cam 30 on the crank disc 5. When a predetermined number of strokes is attained, the meter generates through a pin 32 and electrical contacts 33 and 33, a signal which ceases the operation of the drive element of the pump unit. Thereby, the quantity of the medium supplied from the pump unit corresponds to the receiving capacity of a storage chamber 34 of the discharge element. When the storage chamber during the beginning of the feeding process is not fairly emptied, a negative pressure unit 35 located in a conduit between the discharge element and the valve element 7 operates. Negative pressure of this unit deviates a piston 36 against the pressure of a spring 37, and the flowable medium flows via a conduit 38 into the conduit 10.

In order to discharge the flowable medium from the discharge element, the outlet valve 22 opens under the action of pressure applied to the outlet mouthpiece 23 so that the valve member 26 is lifted from the seal 27 and a throughgoing passage between the storage chamber 34 and the outlet mouthpiece 23 is released. The excessive pressure of the motive gas 19 acts upon the piston 17 from above, and the flowable medium accommodated in the storage chamber is discharged through the spraying nozzle 24 during the period of time of the action upon the outlet mouthpiece 23, in form of a spraying jet 39. The volume of the storage chamber decreases, and the piston 17 moves upwardly in the direction toward the outlet valve with simultaneous sealing of the wall of the container. In order to maintain the pressure a portion of the motive gas 19 is converted from the flowable state into the gaseous state. When the piston 17 abuts against the upper wall of the container, the spraying process terminates.

A new charging process is performed by a press button, or by insertion of the arrangement into a support with simultaneous connection with a storage container 11 and automatic interruption of the current supply.

Figure 2:
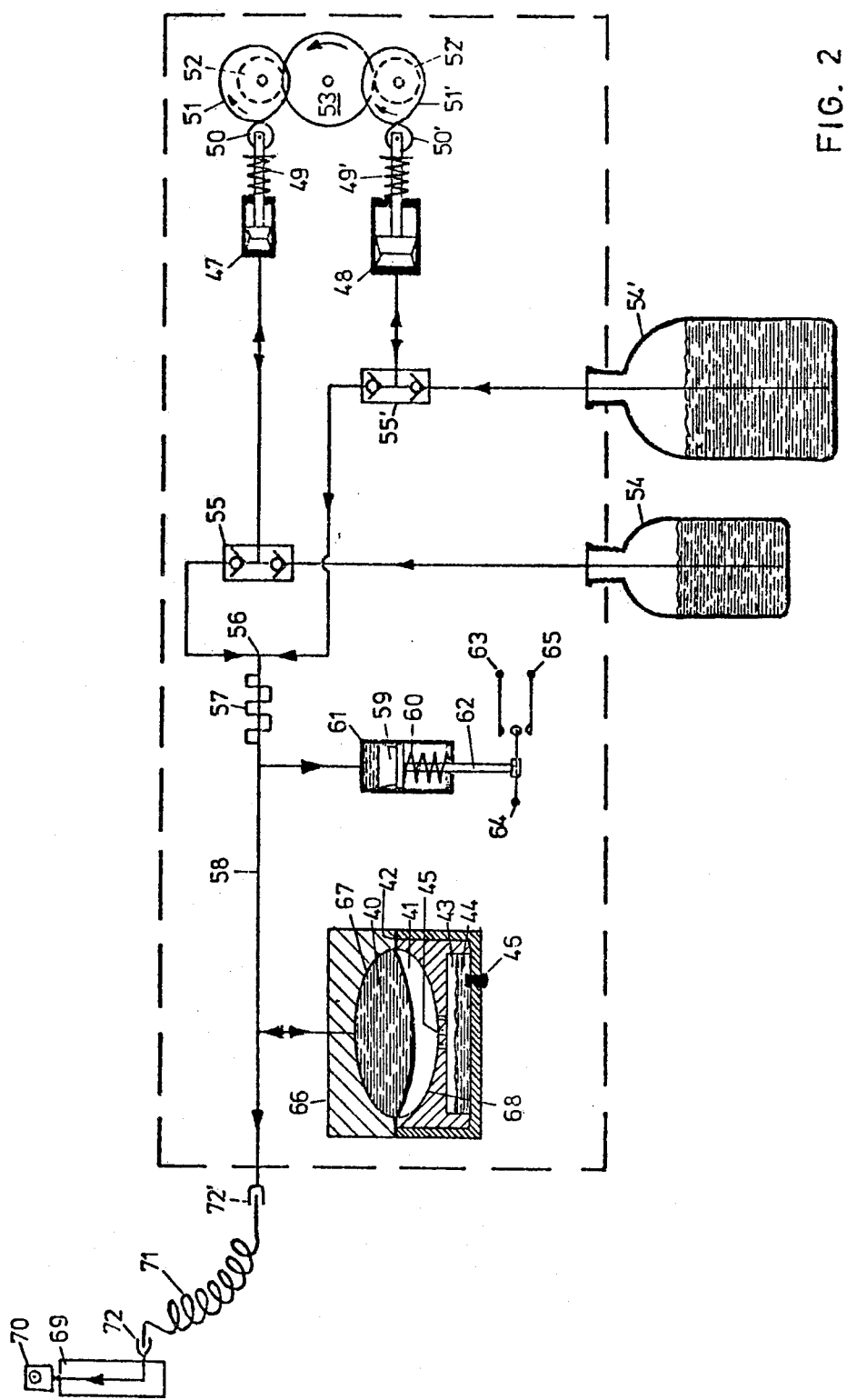
FIG. 2 is a schematic view showing a charge element provided with two pump units and connected with a discharge element having a diaphragm which forms a locking element, wherein an outlet valve is separated from the discharge element and connected with the latter by a movable conduit.
Figure 3:
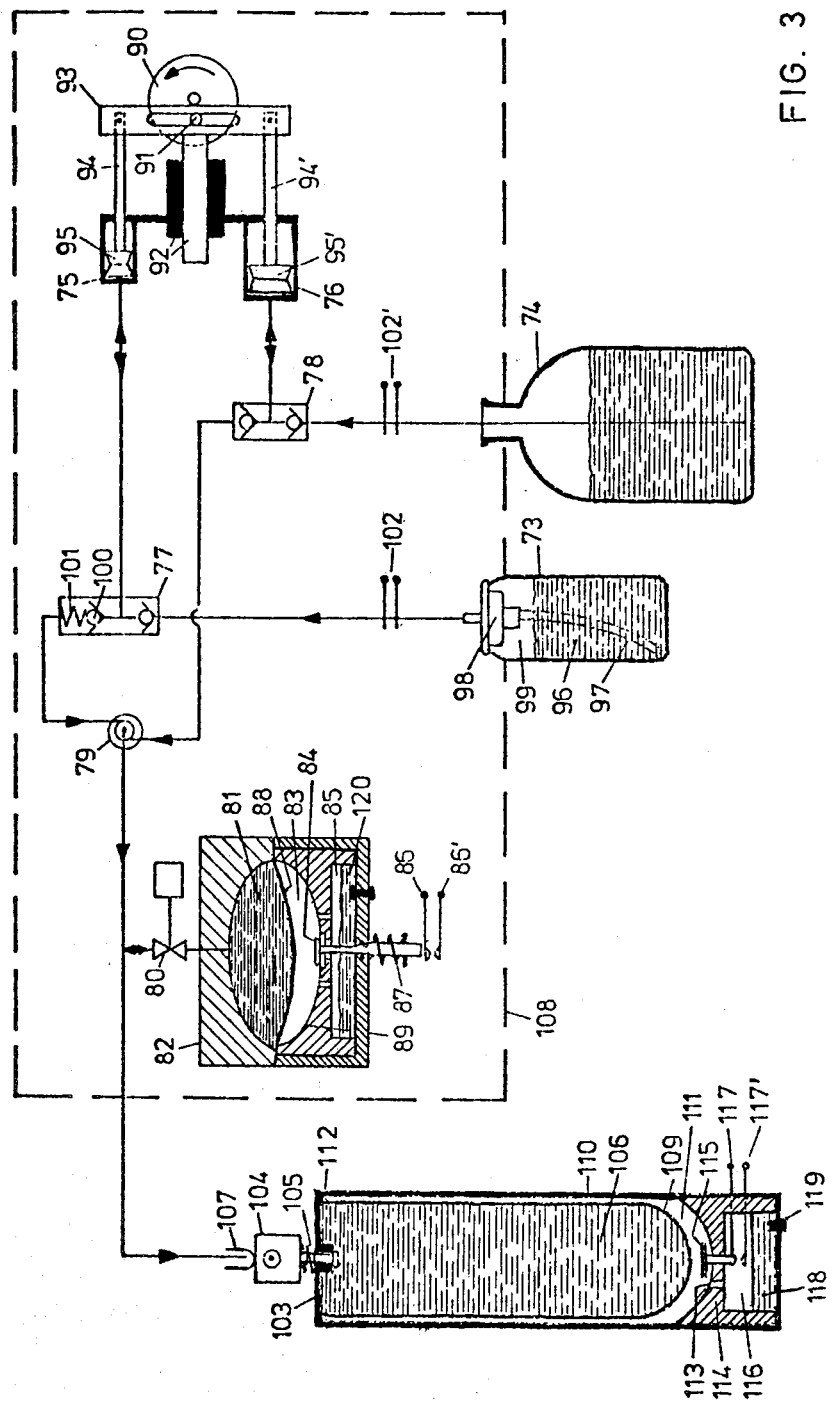
FIG. 3 is a schematic view showing a charge element with two pump units and an intermediate storage element, and a discharge element which is separate from the charge element and provided with a diaphragm-like hollow body forming a locking member.

FIGS. 2 and 3 show another end switching off with the provision of the storage containers and the energy supply to the charge and discharge elements, wherein the pump process can be further performed during the discharge process. In this case, the storage chamber, on the one hand, is emptied slower because of the continuous recharge, and, on the other hand, a uniform, pulsation free and pressure constant discharge of the flowable medium is guaranteed. This is especially important for cosmetic application of the arrangement wherein the generation of noise and the increase of the total weight because of the weight of the storage containers are highly undesirable.

One favorable solution of this problem is shown in FIG. 2. The piston 17 forming a separating member in FIG. 1 is not completely satisfactory in the sense of maintaining its sealing characteristics inasmuch as when the wall of the container is deformed under the outside action, a slow transition of the motive gas into the storage chamber cannot be completely prevented. In the arrangement shown in FIG. 2, the separation between the storage chamber 4 and the gas chamber 14 is performed by a flexible diaphragm or membrane 42 which is clamped between the chambers and seals the latter from one another and outwardly. A lower motive gas chamber 43 contains a flowable component 44 of the motive gas and is connected with the gas chamber 41 for example by openings 45. The motive gas chamber 43 is provided with a filling opening 46 which is closed by a rubber member.

Both pump units 47 and 48 are equipped with pressure springs 49 and 49' and actuated via rollers 50 and 50' and cam discs 51 and 51' from distributing gears 52 and 52' and a drive gear 53 which is driven by a not shown driving element. The pump unit 47 and 48 operate synchronously with one another. Flowable medium accommodated in the storage containers 54 and 54' is displaced by the pump units and through valve elements 55 and 55' in the above-mentioned manner in direction toward the storage chamber 40. The streams of the flowable medium from both pumps are united in 56 and thereafter homogenized by a mixing element 57.

A pressure controller 61 is provided in a conduit 58 or directly in the storage chamber and has a piston 59 and a pressure spring 60. In dependence upon the pressure in the system, the controller 61 actuates the drive element through a piston rod 62 and via switch contacts 63, 64 and 65. When the storage chamber 40 of a discharge element 66 is emptied, the diaphragm abuts against an upper wall 67, the system is pressureless, the contacts 63 and 64 are connected with one another, whereby the driving motor remains switched on via a respective electric circuit until the diaphragm abuts against a lower wall 68 of the container, an excess pressure develops in the system, and the central contact 64 from neutral position contacts the contact 65 and switches off the drive unit.

In order to actuate the drive unit again, it is possible either to release the central contact 64 from the contact 65 or to provide this after full emptying of the storage chamber. The charge element and the discharge element are in this case combined and together form a stationary unit. The discharge of the mixed flowable medium is performed via a separate discharge valve 69 by actuation of an outlet mouthpiece 70 in the above-mentioned manner. The outlet valve is connected via a flexible conduit 71 and a coupling 72, 72' with the discharge element. The mixing ratio of the floable media relative to one another can be varied and adjusted, as shown in the drawing, both by the piston stroke and by the piston area of the pump units 47 and 48. Practically, the pump units may be formed as adjustable slide-in parts, or as automatically adjusted units in accordance with a container code. Thereby, the accurate mixing ratio of the flowable media relative to one another is always guaranteed.

Time which is required for charging a predetermined volume of the storage chamber is determined by the output of the drive unit, inasmuch as the flowable medium must be pumped against the pressure of the motive gas with liquefication of the gas forming components of the motive gas in the storage chamber, which requires a certain quantity of energy. The dimension of the pump unit practically does not influence the charging time. A pump unit which is slowly driven via a respective gearing and is respective big can fill the the storage chamber even during one supply stroke. However, practically on the grounds of both the weight and the dimensions and expenses, a smaller pump unit which provides for faster and greater number or supply strokes is preferable for charging the storage chamber. The operational output of such a pump is maintained on the same grounds as small as possible, and the charging time is located within the range from substantially 30 to 180 seconds for 100 milliliters of the flowable medium.

In order to further reduce the time of charging of the discharge element without increasing the drive output or power, the inventive method is performed as shown in FIG. 3. The flowable media is taken from storage containers 73 and 74 and conveyed via pump units 75 and 76, valve elements 77 and 78, and a mixing chamber 79 operating on stream whirling principle into a storage chamber 81 in an intermediate storage element 82 through a valve 80. The pressure medium is stored in the intermediate storage element 82 until it is to be withdrawn from the same. The intermediate storage element has a construction corresponding to the construction of the discharge element in FIG. 2. However, in addition to the construction of the latter, it contains a sensing element 84 in an upper gas chamber 83, the sensing element actuating contacts 86 and 86' located below a gas chamber 85, and being prestressed by a tension spring 87 in the direction toward a diaphragm 80.

As soon as a storage chamber 81 is filled and the diaphragm abuts against a lower limiting surface 89, the sensing element moves in the direction toward the contacts, closes the same, and provides for the inoperative position of a not shown drive unit having a crank disc 90 with an eccentrically arranged crank pin 91. The crank engages in a longitudinally movable traverse 93 guided by 92 and actuates a movement synchronized drive for pistons 95 and 95' via piston rods 94 and 94'.

The pressure tight storage container 73 contains a liquefied motive gas 96 which is supplied via a lifting pipe 97 and a valve 98 in liquid form to the pipe unit. In order to guarantee that the motive gas cannot be converted into the gaseous state inside the supplied conduits and the pump unit so as to influence the dosing accuracy, the storage container is filled at most to 70 percent of its volume and contains a permanent gas in gas phase 99 which increases the inner pressure by at least 2 bar over the own pressure of the motive gas. An upper valve member 100 of the valve element 77 has a pressure dependent locking function, for example, by the provision of a spring 101. The opening pressure of this valve member is so selected that it is considerably higher than the inner pressure acting in the storage container 73. Thereby, an unintentional over flow of the motive gas in the storage chamber without dosing by the pump unit is reliably prevented. Sensing elements 102 and 102' signal an absence of the flowable medium, for example, during emptying of the container.

In order to charge a discharge element 103, it is connected with the charge element as schematically shown by lines 108, via a not shown valve in an outlet mouthpiece 104, an outlet valve 105, and a coupling 107 which is open into a storage chamber 106. The mixture of the flowable media flows through the valve 80 from the storage chamber 81 of the intermediate storage element 82 under the action of deflection of a flexible diaphragm-like hollow body 109 serving as a separating member. The flowable media flows into the storage chamber 106 of the discharge element 103. An adequate dimension of the cross-section of the conduit between both storage chambers and a considerably higher pressure of a pressure medium 120 in the intermediate storage element than in the discharge element, make possible the charging of the discharge element with for example 100 milliliters of the flowable medium within several seconds. Thereby substantially faster supply of the flowable medium is provided in this arrangement then when the flowable medium is supplied directly by the pump units.

The hollow body 109 is located in a preferably cylindrical pressure-tight container 110, is sealed outwardly and seals a gas chamber 111 in 112. A separating member 114 which connecting openings 113 is provided in the gas chamber. A sealing element 115 extends through the same and acts upon contacts 117 and 117' located in a lower gas chamber 116 and connected with the charge element during the charge process. As soon as the hollow body 109, with its shape assumed in correspondence with the flowable medium in its pressureless state, is fully loaded, it is somewhat stretched during further charging, and thereby acts upon the sensing element 115. The latter closes the contacts 117 and 117' which results in an interruption of the charging process by closing the valve 80 with simultaneous generation of a signal. The discharge element can be separated from the charge element and can be installed at a proper location for discharge of the flowable medium by actuation of the outlet valve via the outlet mouthpiece in the abovedescribed manner. Prior to the reduction of the quantity of the discharging flowable medium, the volume of the storage chamber is also reduced, and the flexible hollow body is elastically deformed until complete emptying of the storage chamber is attained. During the discharge process, the maintenance of the pressure is performed by the constant transmission in the enlarged gas chamber of the liquid motive gas component 118 into the gaseous component. The discharge element has a ventilating opening 119 for the pressure medium.

It will be understood that each of the elements described above, or two or more together, may also find a useful application in other types of constructions differing from the types described above.

While the invention has been illustrated and described as embodied in a method of discharging and applying a flowable medium it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method of discharging and applying flowable medium under pressure, comprising the steps of providing a charge element, and a discharge element having an outlet valve, a storage chamber of a predetermined volume and arranged for receiving the flowable medium, and a gas chamber arranged for accommodating a pressure gas medium and separated from the storage chamber by a displaceable member allowing to vary the volumes of said chambers; feeding the flowable medium from the charge element into the storage chamber of the discharge element, so that the displaceable member displaces in the direction toward the gas chamber, the volume of the storage chamber increases, the pressure gas medium in the gas chamber is compressed and thereby the flowable medium is stored in the storage chamber under pressure; discharging the flowable medium from the storage chamber of the discharge element through the outlet valve by reducing the volume of the storage chamber and increasing the volume of the gas chamber of the discharge element with displacement of the displaceable member in the opposite direction and simultaneous expansion of the gas medium in the gas chamber of the discharge element, said feeding and discharging steps being permanently repeated; and providing a metering element for adjusting the quantity of the flowable medium fed from the charge element into the storage chamber so that said quantity is limited to said predetermined volume.

2. A method as defined in claim 1, wherein said feeding step includes feeding the flowable medium by a pump unit.

3. A method as defined in claim 1, wherein said providing step includes providing the outlet valve with an outlet mouthpiece, said discharging step includes discharging the flowable medium from the outlet valve through the outlet mouthpiece.

4. A method as defined in claim 1, wherein said providing step includes forming said displaceable member as a deflectable diaphragm.

5. A method as defined in claim 1, wherein said providing step includes forming said displaceable member as a movable piston.

6. A method as defined in claim 1, wherein said providing step includes forming said displaceable member as a deformable diaphragm-like hollow body.

7. A method as defined in claim 1, wherein said providing step includes utilizing gas as the gas medium.

8. A method as defined in claim 1, wherein said providing step includes utilizing a mixture of gases as the gas medium.

9. A method as defined in claim 2, wherein said step of feeding the flowable medium by a pump unit includes hand driving of the pump unit.

10. A method as defined in claim 2, wherein said step of feeding the flowable medium by a pump unit includes motor driving of the pump unit.

11. A method as defined in claim 1, wherein said providing step includes providing the gas medium accommodated in the gas chamber of the discharge element as a liquifiable gas medium having a liquid component at a pressure equal between 1 and 15 bar at room temperature.

12. A method as defined in claim 11, wherein said providing step includes containing the liquifiable gas medium in the gas chamber in such amount that even when the entire flowable medium is discharged from the storage chamber and the latter becomes empty, a small portion of the liquid component still remains in the gas chamber in non-evaporated state.

13. A method as defined in claim 2, wherein said feeding step includes utilizing the pump unit which includes a plurality of pumps operating with tact and stroke synchronization, and feeding by the pumps a plurality of flowable components respectively, in a predetermined adjustable ratio relative to one another, so that the flowable components together form the flowable medium.

14. A method as defined in claim 2, wherein said providing step includes utilizing a foamable flowable medium as the flowable medium, said feeding step including feeding the foamable flowable medium simultaneously with feeding of at least one motive gas medium with a predetermined adjustable ratio relative to one another, the steps of feeding of the foamable flowable medium and feeding of the motive gas being performed with tact and stroke synchronization.

15. A method as defined in claim 13, wherein said feeding step includes utilizing a plurality of foamable flowable media as the flowable components, and feeding each of the foamable flowabla media simultaneously with feeding of at least one motive gas medium with a predetermined adjustable ratio relative to one another, the steps of feeding the foamable flowable media and feeding the motive gas media being performed with tact and stroke synchronization.

16. A method as defined in claim 14, wherein said step of feeding at least one motive gas medium includes utilizing at least one motive gas as the motive gas medium.

17. A method as defined in claim 14, wherein said step of feeding at least one motive gas medium includes utilizing at least one mixture of motive gases as the motive gas medium.

18. A method as defined in claim 14, wherein said step of feeding a motive gas includes such feeding that the pressure which is built by the liquified motive gas in the storage chamber of the discharge element is lower than the pressure of the pressure gas medium in the gas chamber of the same.

19. A method as defined in claim 13, wherein said step of feeding a plurality of flowable components includes joining the flowable components with each other before entering the storage chamber of the discharge element.

20. A method as defined in claim 19, wherein said joining step includes joining the flowable components in a mixing chamber.

21. A method as defined in claim 20; and further comprising the step of providing the mixing chamber with a homogenizing member connected in series with the latter.

22. A method as defined in claim 1; and further comprising the step of providing an excess pressure unit between the charge element and the discharge element and acting by the excess pressure unit for preventing the feeding of excessive amount of the flowable medium into the storage chamber of the discharge element.

23. A method as defined in claim 22, wherein said acting step includes switching the feeding of the flowable medium.

24. A method as defined in claim 22, wherein said acting step includes providing a back flow of the flowable medium into the excess pressure unit.

25. A method as defined in claim 1, wherein the storage chamber of the discharge element has a predetermined volume; and further comprising the steps of providing a signalling element arranged in the discharge element and terminating the feeding step by the signalling element in response to attaining by the flowable medium the volume of the storage chamber.

26. A method as defined in claim 14; and further comprising the steps of providing a first supply container accommodating the flowable medium and a second supply container accommodating the liquified motive gas, and interposing an automatically operating return flow blocking element between the pump unit, the supply containers and the storage chamber of the discharge element.

27. A method as defined in claim 1, wherein said providing step includes forming by the charge element and the discharge element, a separate unit.

28. A method as defined in claim 1, wherein said providing step includes coupling the charge element and the discharge element with one another for performing the feeding step, and separating the same from one another for performing the discharging step.

29. A method as defined in claim 1; and further comprising the steps of providing a supply conduit communicating the charge element with the storage chamber of the discharge element, and mounting the outlet valve so that it is separate from the supply comduit.

30. A method as defined in claim 1; and further comprising the steps of providing a supply conduit communicating the charge element with the discharge element, and forming the outlet valve as a coupling for connecting the charge element with the supply conduit.

31. A method as defined in claim 3, wherein said step of providing the outlet mouthpiece of the outlet valve includes exchangeably mounting the outlet mouthpiece.

32. A method as defined in claim 3, wherein said providing step includes mounting the outlet valve with the outlet mouthpiece separate from the discharge element, and connecting the former with the latter by a flexible conduit.

33. A method as defined in claim 1; and further comprising the step of providing an intermediate storage element located between the pump unit and the discharge element.

34. A method as defined in claim 33, wherein said steps of providing the intermediate storage element includes providing the same with a storage chamber and a gas chamber having functions which correspond to the functions performed by the respective chambers of the discharge element, and arranging the intermediate storage element in the charge element.

35. A method as defined in claim 34, wherein the pressure gas medium accommodated in the gas chamber of the intermediate storage element has a specific pressure which is higher than the specific pressure of the pressure gas medium accommodated in the storage chamber of the discharge element.

36. A method as defined in claim 34, wherein the storage chamber of the intermediate storage element has a volume which is at least equal to the volume of the storage chamber of the discharge element.

37. A method as defined in claim 33; and further comprising the steps of providing a signaling element located in the discharge element, and operating the same in response to the feeding step.

38. A method as defined in claim 37, wherein said step of providing a signalling element includes arranging the same in the intermediate storage element.

39. A method as defined in claim 37, wherein said step of providing a signalling element includes arranging the same between the intermediate storage element and the discharge element.

40. A method as defined in claim 37, wherein said operating step includes indicating the feeding step by the signalling element.

41. A method as defined in claim 37, wherein said operating step includes automatically terminating the feeding step by the signalling element.

42. A method as defined in claim 2; and further comprising the step of providing a supply container accommodated the flowable medium, and a detecting element which signals the emptying of the supply container.

43. A method as defined in claim 42, wherein said step of providing a detecting element includes arranging the same in the supply container.

44. A method as defined in claim 42, wherein said step of providing a detecting element includes arranging the same in a supply conduit extending from the supply container to the pump unit.

45. A method as defined in claim 42; and further comprising the step of ceasing the operation of the pump unit by the detecting element in response to the emptying of the supply container.

46. A method as defined in claim 42; and further comprising the step of switching the operation of the pump unit to an additional supply container by the detecting element in response to the emptying of the first-mentioned supply container.

* * * * *